United States Patent [19]

Greif et al.

[11] Patent Number: 4,734,535

[45] Date of Patent: Mar. 29, 1988

[54] PREPARATION OF ALIPHATIC CHLORINE COMPOUNDS

[75] Inventors: Norbert Greif, Bobenheim; Knut Oppenlaender, Ludwigshafen, both of Fed. Rep. of Germany

[73] Assignee: BASF Aktiengesellschaft, Ludwigshafen, Fed. Rep. of Germany

[21] Appl. No.: 30,144

[22] Filed: Mar. 25, 1987

[30] Foreign Application Priority Data

Apr. 5, 1986 [DE] Fed. Rep. of Germany ....... 3611419

[51] Int. Cl.$^4$ ............................................. C07C 17/33
[52] U.S. Cl. .................................. 570/261; 568/606; 568/607; 568/609; 568/610; 568/614; 570/240; 502/164
[58] Field of Search ............... 570/261, 240; 568/614, 568/606, 609, 607, 610; 502/164

[56] References Cited

U.S. PATENT DOCUMENTS 4,605,784 8/1986 Eubanks et al. ..................... 568/614
4,622,431 11/1986 Briody et al. ........................ 568/614

FOREIGN PATENT DOCUMENTS 25829   4/1981 European Pat. Off. .
0180356 5/1986 European Pat. Off. .
0200403 11/1986 European Pat. Off. .
2545659 4/1977 Fed. Rep. of Germany .
2931777 2/1981 Fed. Rep. of Germany ...... 570/261

OTHER PUBLICATIONS

Starks, *J. Am. Chem. Soc.*, vol. 93, pp. 195-199, (1971).

*Primary Examiner*—Michael L. Shippen
*Assistant Examiner*—Bruce D. Gray
*Attorney, Agent, or Firm*—John H. Shurtleff

[57] ABSTRACT

Aliphatic chlorine compounds of the formula $$X-R^1-Cl \qquad \text{I}$$

where $R^1$ is alkylene which may be interrupted by one or more oxygen atoms and which may be substituted by halogen, alkyl or aryl, and X is hydrogen, chlorine or $OR^2$, where $R^2$ is alkyl, cycloalkyl, aryl or aralkyl, are prepared by decarboxylating chloroformic acid esters or diesters at elevated temperatures by decarboxylating in the presence of a quaternary ammonium or phosphonium salt as catalyst.

8 Claims, No Drawings

PREPARATION OF ALIPHATIC CHLORINE COMPOUNDS

The present invention relates to a process for preparing aliphatic chlorine compounds by decarboxylating chloroformic acid esters or diesters at elevated temperatures.

European Pat. No. 25,829 describes the preparation of alkyl chlorides, where the alkyl may also be interrupted by oxygen atoms, by decarboxylating chloroformic acid esters in the presence of trialkylamine hydrochlorides at 90°–170° C. To obtain good conversions, it is necessary to use large amounts of the amine hydrochloride. Advantageously the decarboxylation is carried out in a melt of hydrochloride, and the product isolated from the crude reaction mixture by distillation. In the preparation of nonvolatile alkyl chlorides, the catalyst concentration should not fall below 3% by weight, based on the starting material. If chloroformic acid esters which contain polyether groups are used and the amount of catalyst is reduced to 7.5% by weight, based on the ester, it is true that decarboxylation takes place in the course of a few hours, but the chlorides formed are highly contaminated with byproducts, as shown by IR spectra recorded in the course of the decomposition reaction. The use of large amounts of ammonium salt has the consequence that, in the case of nonvolatile products where direct isolation by distillation is not possible, a technically complicated aqueous extraction becomes necessary to separate off the salts; in addition, there are disposal problems.

It is an object of the present invention to provide a process for decarboxylating aliphatic chloroformic acid esters which requires only small amounts of catalyst and gives high conversions in short reaction times while substantially suppressing the formation of byproducts.

We have found that this object is achieved with a process for preparing an aliphatic chlorine compound of the formula $$X-R^1-Cl \qquad \text{I}$$

where $R^1$ is alkylene which may be interrupted by one or more oxygen atoms and which may be substituted by halogen, alkyl or aryl, and X is hydrogen, chlorine or $OR^2$, where $R^2$ is alkyl, cycloalkyl, aryl or aralkyl, by decarboxylating the corresponding chloroformic acid ester or diester at elevated temperatures, which comprises decarboxylating in the presence of a quaternary ammonium or phosphonium salt as catalyst.

Preferred starting materials are chloroformic acid esters of the formula

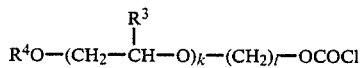

where $R^4$ is alkyl, cycloalkyl, aryl or aralkyl, or is COCl or $-(CH_2)_l OCOCl$, $R^3$ is hydrogen, phenyl or $C_1$- to $C_4$-alkyl which may be substituted by halogen, eg. chlorine or bromine, for example methyl, ethyl, propyl, butyl or chloromethyl, k is 0 to 100, preferably 0 to 50, in particular 0 to 20, and l is 2 to 6.

Preferably $R^4$ is alkyl of 1 to 25, in particular 4 to 20 carbon atoms, $C_5$- or $C_6$-cycloalkyl, phenyl, benzyl or alkyl-substituted phenyl, for example isopropylphenyl, mono-, di- or tri-butylphenyl, amylphenyl, octylphenyl, di-nonylphenyl or dodecylphenyl.

Starting from diesters where $R^4$ is —COCl or $(CH_2)_l$—OCOCl, the corresponding dichlorides are obtained.

Advantageously it is also possible to decarboxylate chloroformic acid esters of the formula $$H-(CH_2)_m-OCOCl \qquad \text{III}$$

where m is for example 1 to 30, in particular 1 to 22, or diesters of the formula $$ClOCO-(CH_2)_m-OCOCl \qquad \text{IV}$$

to give alkyl chlorides. The alkyl chain can additionally carry inert substituents such as halogen atoms, alkyl or aryl, in particular chlorine, bromine, $C_1$-$C_4$-alkyl or phenyl.

The starting materials are obtainable in a conventional manner, for example by reacting the corresponding alcohol with phosgene. They can be expediently prepared in situ.

The decarboxylation is carried out in the presence of a quaternary phosphonium or ammonium salt. Ammonium salts are for example those of the formula

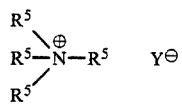

where the radicals $R^5$ are identical or different hydrocarbon radicals of 1 to 20 carbon atoms each, for example $C_1$-$C_{20}$-alkyl, $C_5$- or $C_6$-cycloalkyl, aryl, such as phenyl or p-tolyl or alkylaryl, such as phenyl-substituted $C_1$- to $C_4$-alkyl, and $Y^-$ is the corresponding base of a mineral acid, for example $Cl^-$, $Br^-$, $I^-$, $HSO_4^-$, $NO_3^-$, $HCO_3^-$ or $H_2PO_4^-$. Furthermore, alkyl radicals $R^5$ can also be bonded to one another, for example to form a piperidine ring. Particular preference is given to the quaternary ammonium or phosphonium salts customary for phase transfer catalyzed reactions, for example tetraalkylbenzylammonium or trialkylbenzylammonium salts such as triethylbenzylammonium or tributylbenzylammonium chloride, tetrabutylammonium chloride, bromide or hydrogensulfate, dimethyldicetylammonium chloride or methyltrioctylammonium chloride.

The phosphonium salts which can be used as catalysts have basically the same structure as V with phosphorus in place of nitrogen as the positive center. A specific example is tributylhexadecylphosphonium bromide.

To decompose the chloroformic acid ester, no more than 0.03 to 10, preferably 0.15 to 3, in particular 0.1 to 0.5, percent by weight of catalyst is required, based on the chloroformic acid ester, so that it is possible to use the end-product for subsequent reactions without further working up.

The decarboxylation can be carried out at from 80° to 170° C., preferably from 110° to 140° C., in particular from 120° to 130° C., without solvent or in the presence of an inert aprotic solvent such as, for example, methylene chloride, chloroform, polyethers, dioxane or toluene.

The process is expediently carried out by heating the starting material, which, as the case may be, is prepared in situ, to the reaction temperature and adding the catalyst. The reaction can be monitored for example with the aid of IR spectroscopy. In general, the reaction is complete after from 30 to 120 minutes, and the products can be isolated in a conventional manner, for example by means of distillation in the case of volatile chlorides or in the case of nonvolatile chlorides by extraction and distillative purification. On using low levels of catalyst it is frequently possible to dispense with working up.

The products obtained using the process according to the invention can be used for alkylation reactions, for example for sulfite alkylations or preparing sulfonates.

EXAMPLE 1

Preparation of n-chlorodecane 71 g of a 30% strength phosgene solution in toluene were added dropwise at 10° C. to 103 ml of n-decanol and the mixture was subsequently stirred at 30° C. for 1 h. 1 g of methyltrioctylammonium chloride was then added, and the reaction mixture was slowly heated to 130° C. with $CO_2$ escaping and toluene being distilled off. The residue was stirred at 130° C. for 2 h. In the IR spectrum, the carbonyl absorption band at 1777 cm$^{-1}$ had virtually completely disappeared.

Analysis: Cl value (found)=19.2% (=96% of theory); Cl value (calculated)=20.08%.

EXAMPLE 2

Preparation of

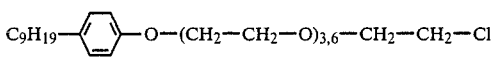

357 g of a 30% strength phosgene solution in toluene were added dropwise at 10° C. to 423 g of

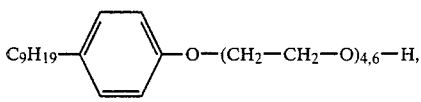

in 80% strength solution in methylene chloride, and the mixture was subsequently stirred at 40° C. for 1 h. After addition of 0.5 g (=0.1% based on the ethoxylate) of methyltrioctylammonium chloride, the reaction mixture was then treated as described in Example 1.

Analysis: Chlorine (found)=8.15%; Chlorine (calculated)=8.04%.

EXAMPLE 3

Preparation of

Cl—CH$_2$—CH$_2$—(O—CH$_2$—CH$_2$)$_8$—O—CH$_2$—CH$_2$—Cl 55 g of phosgene in 150 ml of toluene were added dropwise at 10° C. to 108 g of nonaethylene glycol. The bischloroformic acid ester formed was treated with 0.21 g of tributylhexadecylphosphonium bromide, and the reaction mixture was treated as described in Example 1.

Analysis: Cl value (found)=15% (=92% of theory); Cl value (calculated)=16.24%.

We claim:

1. A process for preparing an aliphatic chlorine compound of the formula $$X-R^1-Cl \qquad I$$

where $R^1$ is alkylene which may be interrupted by one or more oxygen atoms and which may be substituted by halogen, alkyl or aryl, and X is hydrogen, chlorine or $OR^2$, where $R^2$ is alkyl, cycloalkyl, aryl or aralkyl, by decarboxylating the corresponding chloroformic acid ester or diester at elevated temperatures, which comprises decarboxylating in the presence of a quaternary ammonium or phosphonium salt as catalyst.

2. A process as claimed in claim 1, wherein a chloroformic acid ester of the formula $$R^4O-(CH_2-\overset{R^3}{\underset{|}{CH}}-O)_k-(CH_2)_l-OCOCl \qquad II$$

where $R^4$ is $R^2$, —COCl or —(CH$_2$)$_l$OCOCl, $R^3$ is hydrogen, C$_1$–C$_4$-alkyl or phenyl, k is 0 to 100 and l is 2 to 6, is decarboxylated.

3. A process as claimed in claim 1, wherein a chloroformic acid ester of the formula $$H-(CH_2)_m-OCOCl \qquad III$$

where m is 1 to 30, or a diester of the formula $$ClOCO-(CH_2)_m-OCOCl \qquad IV$$

is decarboxylated.

4. A process as claimed in claim 1, wherein the decarboxylation is carried out in the presence of an ammonium salt of the formula

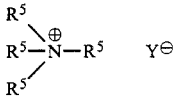

where the radicals $R^5$ are identical or different hydrocarbon radicals of 1–20 carbon atoms each and Y is the corresponding base of a mineral acid.

5. A process as claimed in claim 1, wherein a tetraalkylammonium or benzyltrialkylammonium salt is used.

6. A process as claimed in claim 1, wherein the decarboxylation is carried out in the presence of tributylhexadecylphosphonium bromide.

7. A process as claimed in claim 1, wherein from 0.05 to 10% by weight of the catalyst, based on the chloroformic acid ester, is used.

8. A process as claimed in claim 1, wherein the decarboxylation is carried out at from 80° to 170° C.

* * * * *